United States Patent [19]
Philipp et al.

[11] Patent Number: 5,485,684
[45] Date of Patent: Jan. 23, 1996

[54] DRYER WITH PRECISION BALANCE

[75] Inventors: Florian Philipp, Bertschikon; Alfred Hautle; Reto Nuesch, both of Greifensee; Beat Straub, Uster, all of Switzerland

[73] Assignee: Mettler-Toledo AG, Greifensee, Switzerland

[21] Appl. No.: 163,925

[22] Filed: Dec. 8, 1993

[30]    Foreign Application Priority Data

Feb. 16, 1993 [CH] Switzerland ............... 00472/93

[51] Int. Cl.⁶ ....................................... F26B 19/00
[52] U.S. Cl. ................... 34/226; 34/308; 34/202; 177/245
[58] Field of Search ............ 34/202, 536; 177/245, 177/180, 200

[56]             References Cited

U.S. PATENT DOCUMENTS

| 3,032,132 | 10/1959 | Ohaus . | |
|---|---|---|---|
| 4,666,007 | 5/1987 | Knothe et al. | 177/245 |
| 4,889,201 | 12/1989 | Oldendorf et al. . | |
| 5,064,009 | 11/1991 | Melcher et al. . | |
| 5,249,367 | 10/1993 | Nafziger et al. | 34/202 X |

FOREIGN PATENT DOCUMENTS

| 0145665 | 6/1985 | European Pat. Off. . |
| 3814959A1 | 11/1989 | Germany . |

*Primary Examiner*—Henry A. Bennett
*Attorney, Agent, or Firm*—Friedrich Kueffner

[57]             ABSTRACT

A drying apparatus includes a built-in precision balance for determining the moisture content of material to be weighed. The apparatus includes a weighing dish for receiving the material. The weighing dish is connected to a load-receiving member of the measuring cell of the balance. A heat source is arranged above the weighing dish for heating the material. During drying, the weighing dish is located within the housing. The weighing dish can be moved in and out of the housing for charging and weighing-in of the material.

13 Claims, 4 Drawing Sheets

DRYER WITH PRECISION BALANCE

BACKGROUND OF THE INVENTION

1. Field of the Invention

The present invention relates to a dryer with a built-in precision balance for determining the moisture content of material to be weighed. The dryer includes a weighing dish for receiving the material to be weighed. The weighing dish is connected to a load-receiving unit of the measuring cell of the balance. The dryer further includes a heat source arranged above the weighing dish for heating the material to be weighed. During drying, the weighing dish is arranged within the housing. The dryer further has means for making the weighing dish accessible for charging the weighing dish and for weighing the material to be weighed.

2. Description of the Related Art

For determining the moisture content of a product, a sample of the product is dried and the weight of the sample is measured before and after the drying procedure, and possibly also during the weighing procedure. The drying procedure is preferably carried out directly on a balance in order to avoid losses during the manipulation of the material to be dried and to be able to carry out the determination as quickly as possible.

DE-A1-3814959 discloses a moisture measuring device in which several samples are placed on a rotary plate in a stove and are individually placed on a balance for weighing. In such a device, weighing-in must be carried out on a second balance before placing the samples on the plate and before inserting the plate in the stove. In addition, each sample must be identified in order to avoid mix-ups with other samples.

Since the work surfaces in kitchens and in laboratories are usually very narrow, so that by the permanent presence of a balance which is only used occasionally the necessary surface area utilized by this balance cannot be used for other purposes, EP-A-0145665 proposes a household or laboratory balance which is placed in a conventional standard drawer and can be pushed under the work surface of a work table when it is not used. This balance arrangement makes it possible to keep the work surface free even during the weighing procedure because weighing is carried out in the pulled-out drawer in front of the work surface. Simultaneously, it is made possible that the balance does not have to be newly leveled on the work surface before each use. Also, contamination is avoided while the balance is not in use. This known balance is preferably elastically suspended in the drawer, so that impacts during movement of the drawer can be kept away from the balance unit. In order to safely ensure that the balance is switched off in the pushed-in state, additional means are proposed for allowing current only to be supplied when the drawer is in the fully pulled-out position.

Consequently, this known balance arrangement cannot be used for a weighing procedure with a precision balance in a space which is closed off from the surroundings and excludes air flows. On the one hand, the surface of the weighing dish is located immediately below the work surface, so that it is not possible to build up a closed space above the weighing dish and, on the other hand, the balance is not in operation as soon as the balance is pushed in by a certain distance. In addition, the control and display instruments are pushed together with the balance under the work surface, so that these instruments also do not cover the work surface and are protected.

In another already known dryer (METTLER LP 16 "Infrared Dryer"), a precision balance is mounted in the dryer, wherein the weighing dish is located in a stove or drying chamber. The stove chamber is provided with a swivel-mounted cover for charging the weighing dish with the material to be weighed. The heating element is additionally mounted in the cover. An infrared radiator is used in this known drying stove as a heating element. This drying stove meets the requirements with respect to weighing accuracy because weighing-in of the moist material to be dried and weighing of the dried material can take place directly on the balance. However, it is not very easy to charge the weighing dish which is located within the housing and is only accessible through the opening released by the open cover, and, if necessary, to remove any excess material which has been placed on the weighing dish during weighing-in.

SUMMARY OF THE INVENTION

Therefore, it is the primary object of the present invention to provide a drying stove with built-in balance whose weighing dish is easily accessible for charging and weighing-in the material to be weighed before drying and for the removal of the material from the weighing dish.

In accordance with the present invention, the weighing dish is constructed in such a way that it can be moved in and out of the housing for charging and weighing-in of the material to be weighed.

The dryer according to the present invention makes it possible for the operator to charge the weighing dish from the front as well as from the side because the weighing dish is mounted so as to be completely movable out of the housing. The measuring cell remains connected to the weighing dish via the load receiving means even in the moved-out state, so that weighing procedures can be carried out during the charging and drying process. Since the weighing dish is freely accessible from three sides, left-handed persons can also use the dryer without problems.

The pulled-out weighing dish is located on a low level above the support surface of the drying stove, so that weighing-in can be carried out with the hand resting on the support surface.

A viewing glass mounted in the housing above the weighing dish makes it possible to observe the material to be dried during the drying procedure. During the procedure, the material is illuminated by a ring-shaped halogen lamp.

The various features of novelty which characterize the invention are pointed out with particularity in the claims annexed to and forming a part of the disclosure. For a better understanding of the invention, its operating advantages, specific objects attained by its use, reference should be had to the drawing and descriptive manner in which there are illustrated and described preferred embodiments of the invention.

DETAILED DESCRIPTION OF THE PREFERRED EMBODIMENTS

Figure 1:
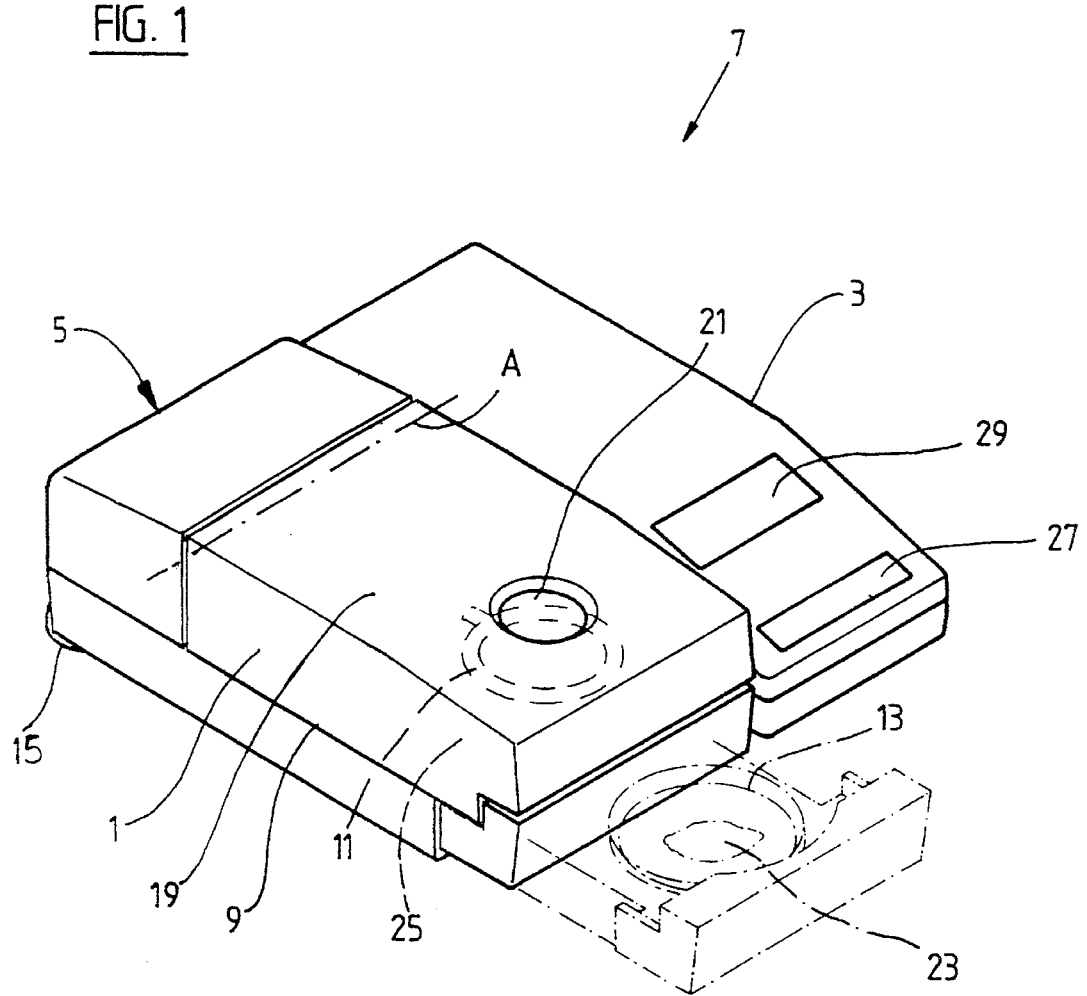
FIG. 1 is a perspective view of a dryer with a weighing dish shown in the pulled-out state in broken lines.

As shown in FIG. 1 of the drawing, a drying apparatus 7 has a housing 5 composed of two parts 1 and 3. Mounted in part 1 are a balance or weighing unit 9 and a heat source 11 above the weighing dish 13 of the balance 9. The part 3 of the housing is arranged laterally adjacent the part 1. The part 3 contains the control and display elements. Electronic components for the balance 9 may also be mounted in the part 3.

The front portion of the upper part of part 1 is constructed as a cover 19 and can be swung upwardly about a horizontal axis A. An inspection glass 21 may be placed in the cover 19 to make it possible to view the inserted weighing dish 13 and the material 23 placed on the weighing dish 13. The inspection glass 21 is located concentrically relative to the heat source 11. In the illustrated embodiment, the heat source 11 is an essentially ring-shaped halogen lamp which heats and illuminates the drying space 21 located between the weighing dish 13 and the cover 19.

A keyboard 27 and a display area 29 are arranged on the upper side of the part 3 for controlling the functions of the balance 13 and the drying stove. The configuration of the control and display elements is not explained in detail since they are not subject of the invention.

The drying apparatus 7 is supported on legs 15 for exactly horizontally leveling the drying apparatus 7.

Figure 2:
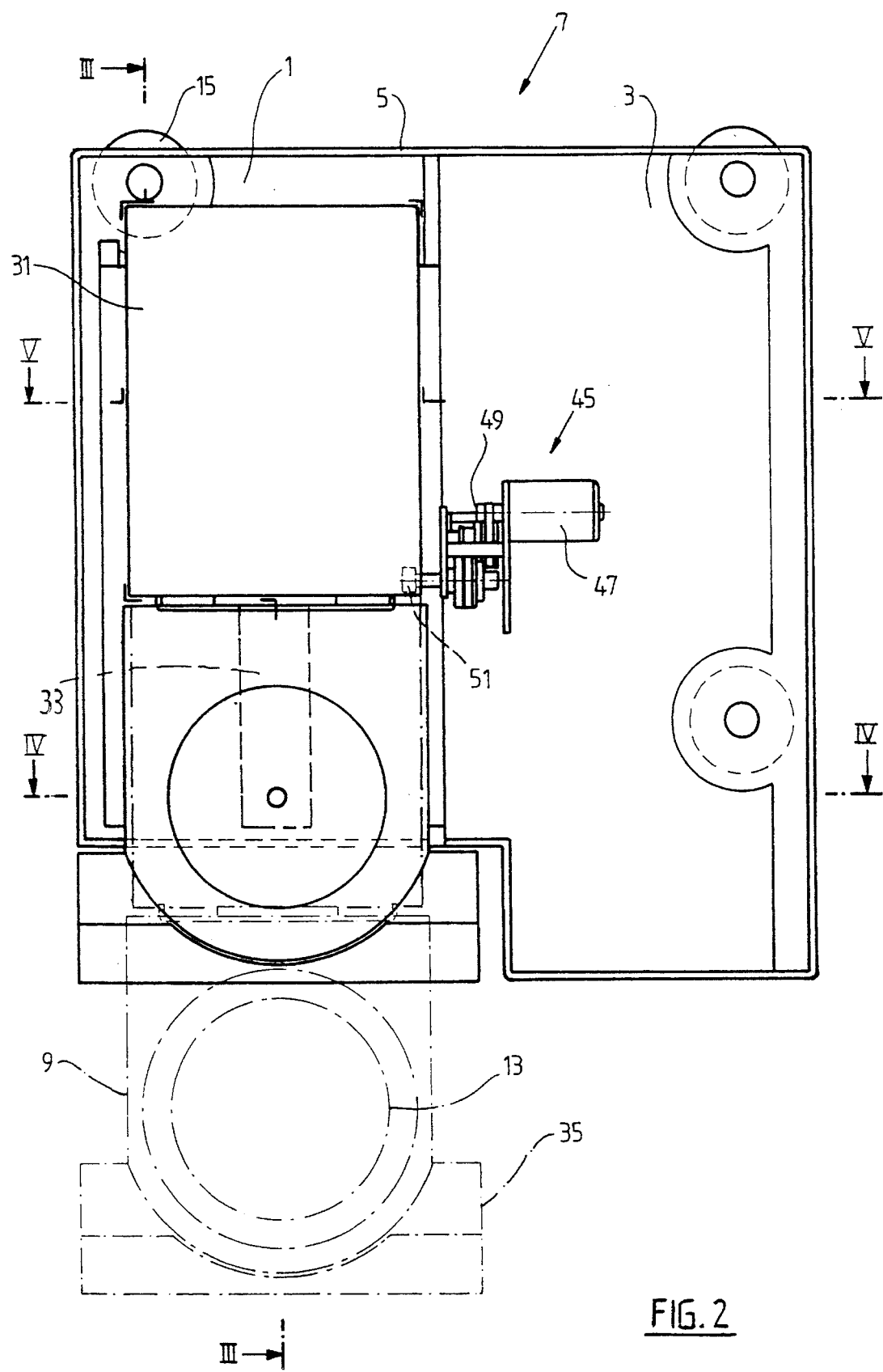
FIG. 2 is a top view of the dryer of FIG. 1.
Figure 5:
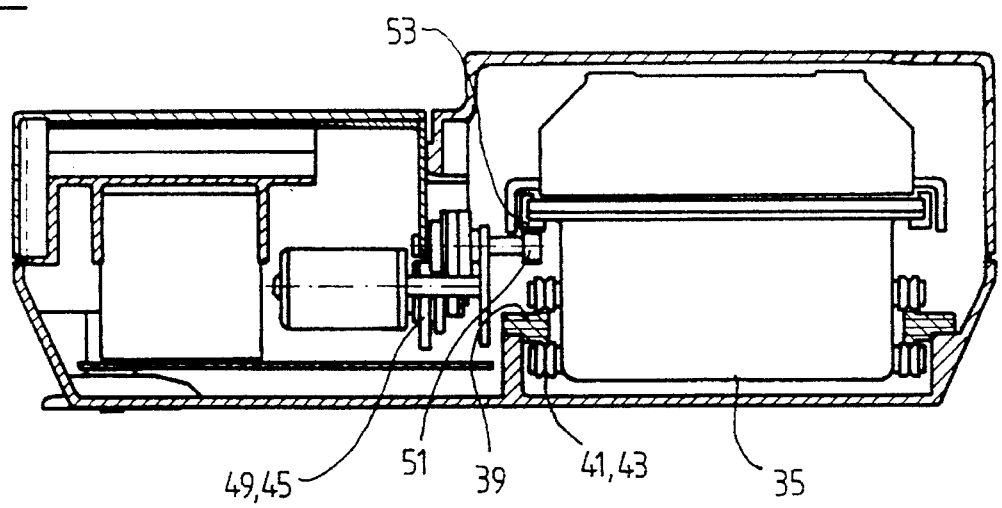
FIG. 5 is a cross-Sectional view of the dryer taken along sectional line V—V in FIG. 2.

The balance 9 including the measuring cell 31 and the load receiving means 33 which carries the weighing dish 13 are placed in a drawer-like pull-out member 35 and are movably mounted on a linear guide 37. As shown in FIGS. 2–5, the linear guide 37 includes a pair of guide rails 39 which are fastened to the housing 5 and interact with rollers 41 connected to the pull-out member 35. The rollers 41 are preferably arranged in pairs one above the other, so that an essentially play-free support is effected from below as well as from above. The lateral guidance of the pull-out member 35 can be ensured by grooves 43 in the circumferential surfaces of the rollers 41 if the guide rails 39 have correspondingly shaped rib-like running surfaces determined for engaging in the grooves 43. The pull-out member 35 can be pushed in and out of the housing 5 either manually or by means of a motor drive 45, as illustrated in FIGS. 2 and 5. The drive 45 has an electric motor 47 with a gear unit 49. A pinion 51 is mounted on the drive side of the gear unit 49. The pinion 51 meshes with a rack 53 fastened to the pull-out member 35. The rack 53 may be a component of a trough-shaped pull-out member 35.

Figure 6:
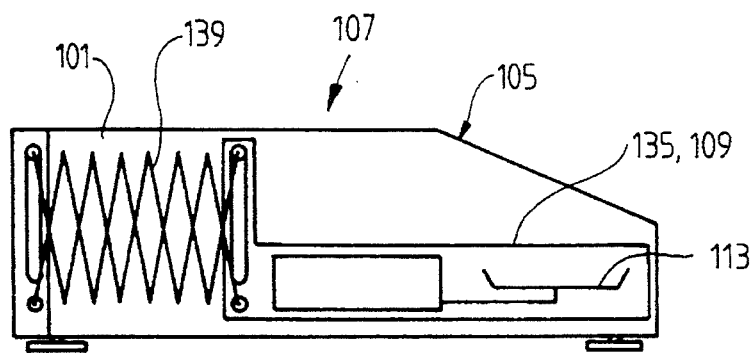
FIG. 6 is a schematic sectional view of another embodiment of the invention with a scissors-type means for longitudinal guidance.

As shown in FIG. 6, instead of guide rails, it is also possible to provide scissors-type guide means 139 whose rearward ends are fastened fixedly at the bottom and vertically displaceably at the top on part 101 of the housing 105 and whose front ends support the balance 109 or the pull-out member 135 receiving the balance 109.

Figure 7:
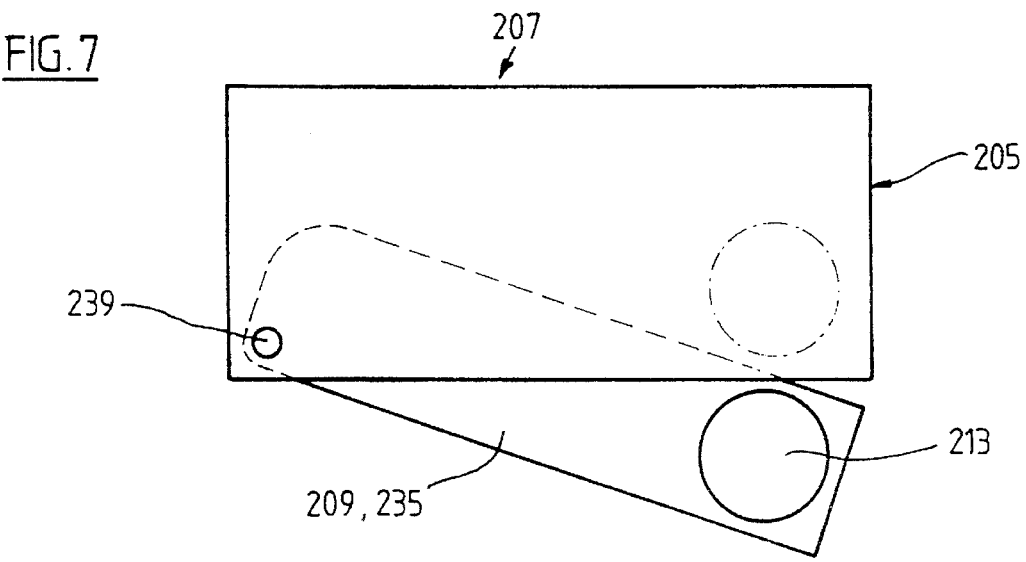
FIG. 7 is a schematic sectional view of another embodiment of the invention with a balance unit which can be swung about a vertical axis.

Another alternative to the linear guidance is the swingable support of the pull-out member 235 shown in FIG. 7. For this purpose, the pull-out member 235 is hinged to a vertical shaft 239 and, as a result, can be laterally swung out to such an extent until the weighing dish 213 is located completely outside of the housing 205.

In the embodiments of the invention shown in FIGS. 6 and 7, it is also possible to use electrical drives, not shown, for pulling out or swinging the pull out member 135 or 235.

Figure 3:
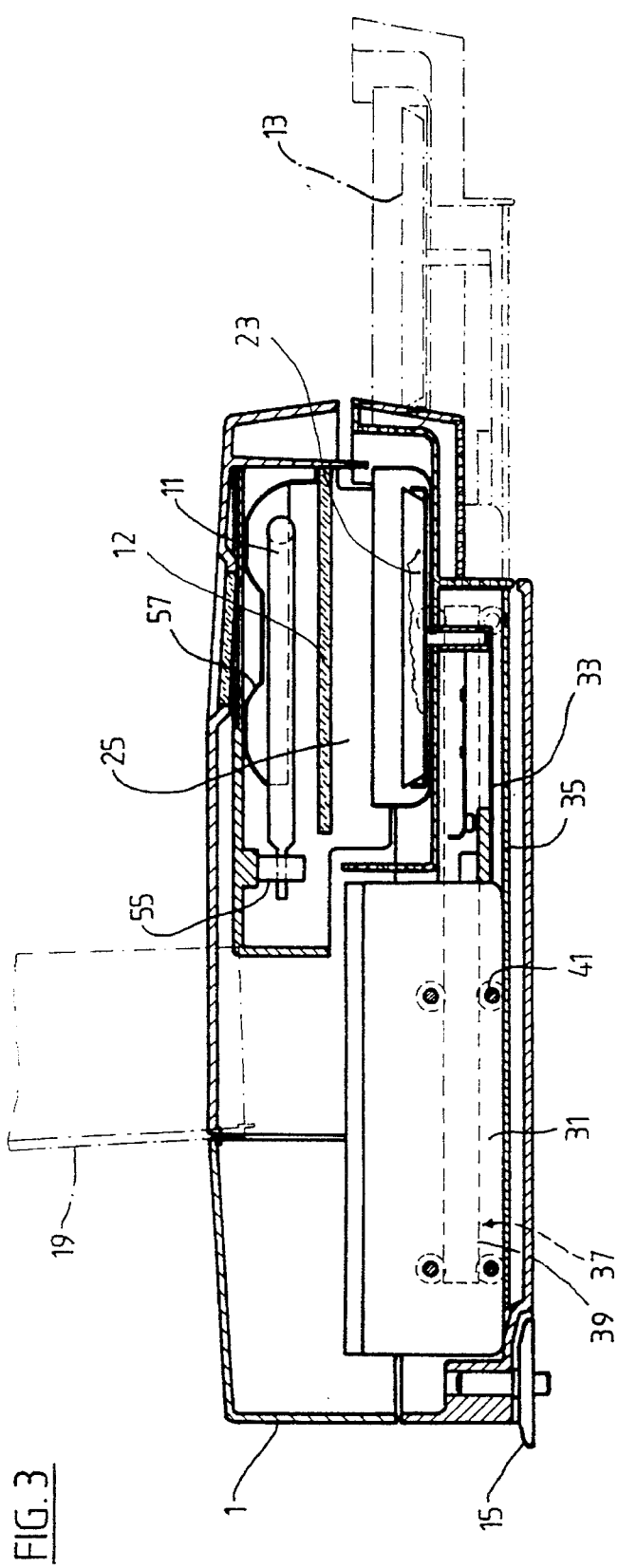
FIG. 3 is a cross-sectional view of the dryer taken along sectional line III—III in FIG. 2, with the pulled-out weighing dish shown in dash-dot lines.
Figure 4:
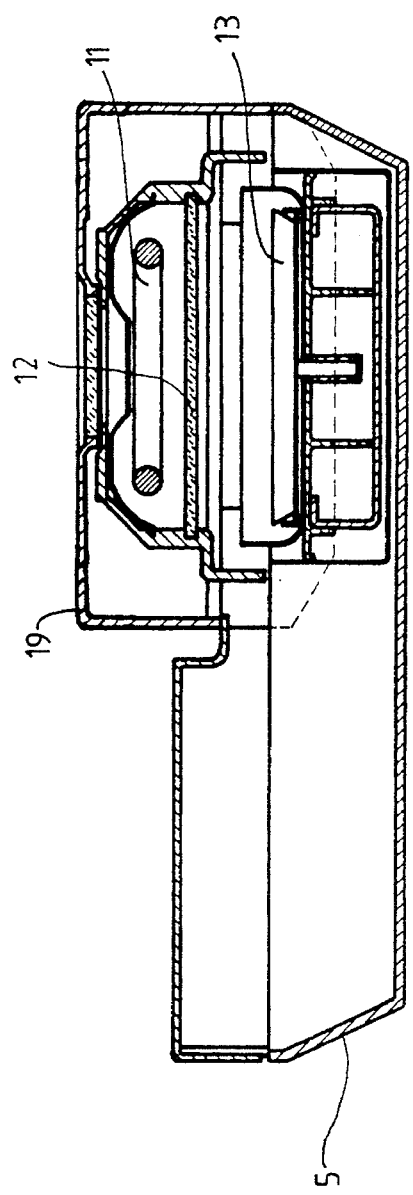
FIG. 4 is a cross-sectional view of the dryer taken along sectional line IV—IV in FIG. 2.

As shown in FIG. 3 of the drawing, the swingably mounted cover 19 includes on an insulated bracket 55 the heat source 11, for example, a ring-shaped halogen lamp. A reflector 57 is mounted above the heat source 11 for reflecting and focusing the thermal radiation onto the weighing dish 13, and for preventing excessive heating of the surface of the cover 19. The reflector 57 may be constructed ring-shaped, especially if an inspection glass 21 is provided in the cover 19.

During operation of the drying apparatus 7, the cover 19 remains always closed. The cover 19 is only opened for cleaning the reflector 57 or for replacing the heat source 11.

A protective glass 12 may be fastened on the cover 19 underneath the heat source 11 for protecting the halogen lamp against contact by the operator and against contact with the material 23 being weighed. The protective glass 12 may also serve as a filter for protecting, for example, UV-sensitive materials against damaging effects from this radiation.

In the following, the operation of the dryer 7 will be explained in more detail in connection with the embodiment of the invention shown in FIGS. 1–5.

The pull-out member 35 is pulled out manually or by pressing a button until the weighing dish 13 is located completely outside of the housing 5. In this position, the weighing dish 13 is not only freely accessible from the front, but also from both sides. Charging and weighing-in of the material 23 can now be easily carried out because the balance 9 is always ready for weighing and taring. Taring is usually carried out before weighing-in of the material. As a result of the precise guidance of the pullout member 35, the weighing procedures can be carried out inside and outside of the housing 5 with the required accuracy without further taring.

As soon as the material 23 has been weighed in, the pull-out member 35 is returned into the housing 5 and the drying procedure (moisture removal from the material 23) can begin by switching on the heat source 11. The weight loss over time can be observed continuously on the display area 29 or can be recorded by a printer, not shown. The return of the weighing unit 9 can be effected, for example, by pressing a start button. After the moisture removal, i.e. the drying process has been concluded, the pull-out member 35 is again pulled out of the housing 5 for removing the dried material 23. It is safely ensured that the material 23 is not spilled within the drying stove 7.

The manner of operation of the dryer 107 of FIG. 6 is analogous to the manner of operation of the dryer shown in FIGS. 1–5.

The dryer 207 shown in FIG. 7 differs in its operation from the dryers described above in that the pull-out member 235 is not pulled out in a linear movement, but by a swinging movement about the axis 239, so that the weighing dish 213 is pulled out laterally when the axis 239 is provided at the rear side of the dryer 207. If the axis were to be arranged on the right-side of the dryer, which is also easily possible, the weighing dish 213 would be pulled out or swung out at the front, so that the weighing dish is accessible from both sides also in this embodiment of the invention.

The invention is not limited by the embodiments described above which are presented as examples only but can be modified in various ways within the scope of protection defined by the appended patent claims.

We claim:

1. A drying apparatus with a built-in precision balance for determining the moisture content of material to be weighed, the apparatus comprising a housing, a weighing dish for receiving the material, the balance having a measuring cell, a load-receiving means being connected to the measuring cell, a heat source being mounted above the weighing dish for heating the material, the weighing dish being located within the housing during drying, and means for moving the weighing dish in an essentially horizontal plane into and out of the housing for making the weighing dish accessible for charging and weighing-in of the material.

2. The drying apparatus according to claim 1, wherein the measuring cell, the load receiving means and the weighing dish form a weighing unit, the entire weighing unit being movable by the means for moving the weighing dish.

3. The drying apparatus according to claim 2, comprising a parallel guide means, the weighing unit being movable out of the housing on the parallel guide means.

4. The drying apparatus according to claim 2, comprising a swinging means, the weighing unit being movable out of the housing on the swinging! means.

5. The drying apparatus according to claim 3, wherein the parallel guide means includes at least one guide rail mounted in the housing, further comprising a pull-out member supporting the weighing unit, the pull-out member being supported on the guide rail.

6. The drying apparatus according to claim 3, wherein the parallel guide means comprises at least one scissors-type longitudinal guide member having a rearward end and a forward end, the rearward end being connected to and guided on the housing, and the forward end supporting the weighing unit.

7. The drying apparatus according to claim 4, wherein the weighing unit is swingable about a vertically extending shaft.

8. The drying apparatus according to claim 1, wherein the housing comprises a cover, the cover being connected to the housing so as to be swingable about a horizontal axis, the heat source being mounted on the cover above the weighing dish.

9. The drying apparatus according to claim 1, wherein the heat source is a halogen lamp.

10. The drying apparatus according to claim 9, wherein at least portions of the halogen lamp are ring-shaped, and wherein the ring-shaped portion is arranged concentrically relative to the weighing dish.

11. The drying apparatus according to claim 1, wherein the housing comprises above the weighing dish an inspection glass for observing the material when the weighing dish is pushed into the housing.

12. The drying apparatus according to claim 1, comprising a protective glass mounted between the heat source and the weighing dish.

13. The drying apparatus according to claim 12, wherein the protective glass comprises a protective filter against UV-radiation.

* * * * *